United States Patent [19]

Gilkerson et al.

[11] Patent Number: 4,954,160
[45] Date of Patent: Sep. 4, 1990

[54] OXIMINO ETHER COMPOUNDS

[75] Inventors: Terence Gilkerson, Canterbury; Robert W. Shaw, Sittingbourne, both of England

[73] Assignee: Shell Internationale Research Maatschappij, B.V., The Hague, Netherlands

[21] Appl. No.: 247,273

[22] Filed: Sep. 21, 1988

[30] Foreign Application Priority Data

Sep. 29, 1987 [GB] United Kingdom ................. 8722838

[51] Int. Cl.$^5$ ............................................. A01N 43/40
[52] U.S. Cl. ........................................ 71/88; 564/256; 564/85; 564/86; 564/87; 560/107; 560/250; 560/251; 558/412; 558/414; 549/442; 71/98; 71/103; 71/105; 71/106; 71/118; 71/121
[58] Field of Search .................... 71/88, 103, 121, 106, 71/98, 105, 118; 564/256, 85, 86, 87; 560/107, 251, 250; 558/412, 414; 549/442

[56] References Cited

U.S. PATENT DOCUMENTS

| | | | |
|---|---|---|---|
| 3,989,737 | 11/1976 | Sawaki et al. | 564/256 |
| 4,440,566 | 4/1984 | Luo | 564/256 |
| 4,652,303 | 3/1987 | Watson et al. | 564/256 |
| 4,666,510 | 5/1987 | Watson et al. | 564/256 |
| 4,806,141 | 2/1989 | Watson et al. | 564/256 |

FOREIGN PATENT DOCUMENTS

| | | | |
|---|---|---|---|
| 82694 | 6/1983 | European Pat. Off. | 71/121 |
| 85530 | 8/1983 | European Pat. Off. | 71/121 |
| 86588 | 8/1983 | European Pat. Off. | 71/121 |
| 172551 | 2/1986 | European Pat. Off. | 71/121 |
| 218233 | 4/1987 | European Pat. Off. | 71/121 |
| 51-013756 | 2/1976 | Japan | 71/121 |
| 58-077848 | 5/1983 | Japan | 71/121 |
| 2179352 | 3/1987 | United Kingdom | 71/121 |

Primary Examiner—James H. Reamer

[57] ABSTRACT

The invention provides compounds of the general formula

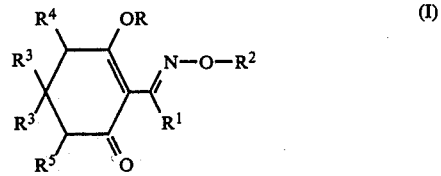

wherein

R represents a hydrogen atom, or an optionally substituted alkyl or acyl group, or an alkenyl or alkynyl group or an inorganic or organic cation;

$R^1$ represents an alkyl, haloalkyl, alkenyl, alkynyl or optionally substituted aralkyl or phenyl group;

$R^2$ represents an optionally substituted alkyl or phenalkyl group or a cycloalkyl, alkenyl, haloalkenyl or alkynyl group;

each $R^3$ represents an optionally substituted alkyl group;

one of $R^4$ or $R^5$ represents a hydrogen atom or an alkyl group while the other of $R^4$ and $R^5$ represents an optionally substituted phenyl group; together with their use as herbicides and their preparation using novel intermediates.

21 Claims, No Drawings

OXIMINO ETHER COMPOUNDS

This invention relates to novel oximino ether compounds, to their use as herbicides, to their preparation, and to intermediates therefor, and their preparation.

In accordance with the present invention there are provided compounds of the general formula

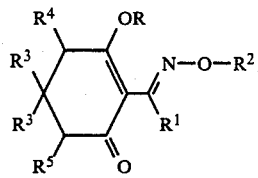

(I)

wherein

R represents a hydrogen atom, or an optionally substituted alkyl or acyl group, or an alkenyl or alkynyl group or an inorganic or organic cation;

$R^1$ represents an alkyl, haloalkyl, alkenyl, alkynyl or optionally substituted aralkyl or phenyl group;

$R^2$ represents an optionally substituted alkyl or phenalkyl group or a cycloalkyl, alkenyl, haloalkenyl or alkynyl group;

each $R^3$ represents an optionally substituted alkyl group;

one of $R^4$ and $R^5$ represents a hydrogen atom or an alkyl group; while the other of $R^4$ and $R^5$ represents an optionally substituted phenyl group.

In general terms it may be stated that, unless otherwise specified herein, a (halo)alkyl group, including the alkyl linkage of a phenalkyl group, suitably has 1–6, especially 1–4 carbon atoms; a (halo) alkenyl or alkynyl group has 2–6, especially 2–4 carbon atoms. Haloalkyl and haloalkenyl groups are suitably substituted by 1–3 halogen atoms. Fluorine and chlorine are the preferred halogen atoms. A cycloalkyl group preferably has 3–6 carbon atoms, and is most preferably cyclopropyl. An optionally substituted alkyl group may suitably be substituted by one or more moieties independently selected from halogen atoms and $C_{1-6}$ alkoxy, $C_{1-6}$ alkylthio, ($C_{1-6}$alkoxy)carbonyl, and optionally substituted phenyl groups. An optionally substituted phenyl group may suitably be substituted by one or more moieties independently selected from halogen atoms and nitro, cyano, $C_{1-6}$ alkyl, $C_{1-6}$ haloalkyl, $C_{1-6}$ alkoxy, $C_{1-10}$ alkylene dioxy, $C_{1-6}$ alkylthio and $C_{2-6}$ alkenylthio and amino, acetamido, mono($C_{1-4}$) alkylamino and di($C_{1-4}$-alkyl)amino groups, and acyl groups. An acyl group may be defined as a group formed by removal of —OH from an organic acid. Suitable acyl groups include $C_{2-6}$ alkanoyl and optionally substituted benzoyl groups, and sulphonyl groups, for example alkylsulphonyl and optionally substituted phenylsulphonyl groups, and sulphonamido groups of formula $SO_2NQ^1Q^2$ where each of $Q^1$ and $Q^2$ independently represents a hydrogen atom or an alkyl group. Suitable as cations are alkali and alkaline earth metal ions, transition metal ions and optionally substituted ammonium ions, optional substituents being 1–4 groups independently selected from optionally substituted alkyl, phenyl and phenalkyl groups.

Preferably, R represents a hydrogen atom.

Preferably, $R^1$ represents a $C_{1-6}$ alkyl group, especially ethyl or n-propyl, or an optionally substituted aralkyl group.

Preferably, $R^2$ represents a $C_{1-6}$ alkyl group, optionally substituted by a halogen atom (e.g. fluorine or chlorine) or an alkoxy group (e.g. methoxy), or $C_{2-6}$ alkenyl, optionally substituted by a halogen atom, such as a chloroallyl group especially trans chloroallyl.

Most preferably $R^2$ represents $C_{1-4}$ alkyl, especially ethyl; or allyl.

Preferably, each $R^3$ represents a methyl group.

Preferably, one of $R^4$ and $R^5$ represents hydrogen and the other of $R^4$ and $R^5$ represents a phenyl group optionally substituted by 1–5 moieties independently selected from halogen atoms and $C_{1-6}$ alkyl, haloalkyl alkoxy and alkylene dioxy groups, and sulphonamido groups.

It should be noted that when R is hydrogen the compounds of the invention may exist in any one of tautomeric forms as shown below:

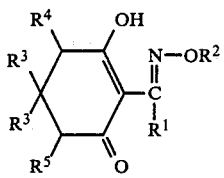

In this specification, recitation of any one of these forms denotes any tautomer or the tautomer mixture of which the recited form is a constituent. In relation to precursors, the reaction of any one tautomer also denotes any tautomer or the tautomer mixture.

The compounds of the invention may be prepared by a variety of methods and in a further aspect the invention provides methods for the preparation of compounds of formula I.

Conveniently the preparation of the compounds of the invention can be considered in three or four parts.

Part A involves the formation of a 4(or 6)-(optionally substituted phenyl)cyclohexane-1,3-dione of formula II. This reaction is suitably carried out by reacting together compounds of formulae III and IV

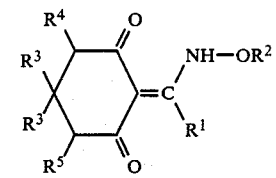

where $R^6$ represents an alkyl, preferably methyl or ethyl group, in the presence of an alkali metal alkoxide, for example sodium methoxide or ethoxide. The reaction suitably takes place in the presence of an inert organic solvent, for example benzene, toluene or xylene, at ambient or elevated temperature, for example 20°–150° C., preferably in the range 50° C. to the reflux temperature.

The starting materials III and IV are known or derivable from known compounds by standard methods.

Part B involves the acylation of a compound of formula II to give a 2-acyl-4(or 6)-(optionally substituted phenyl)-3-hydroxy cyclohex-2-ene-1-one of formula V

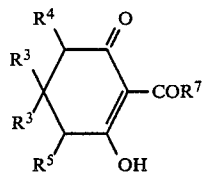
(V)

where $R^7$ represents an alkyl group. This may be effected by reacting a 4(or 6)-(optionally substituted phenyl)-cyclohexane-1,3-dione of formula II with an acid $R^7COOH$ and/or a salt, anhydride or acid chloride thereof. The reaction suitably takes place in the presence of a polar organic solvent, for example pyridine or acetonitrile, at an elevated temperature, for example 40° C. to 150° C., in the presence of a Lewis acid, for example zinc chloride, zinc cyanide, aluminium chloride, 4-(N-dimethylamino)pyridine (DMAP), or a polymeric Lewis acid catalyst comprising at least one pyridylamino functional group, as described in AU 652992.

Alternatively, and preferably, the acylation may be carried out by reacting a 4(or 6)-(optionally substituted phenyl)cyclohexane-1,3-dione of formula II with an acid $R^7COOH$ and/or a salt, anhydride or acid halide thereof, in the presence of an amine base/solvent, suitably triethylamine or pyridine, to give an intermediate O-acyl derivative of formula VI

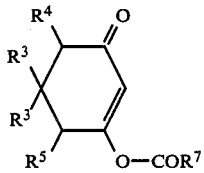
(VI)

and then rearranging the intermediate of formula VI with a Lewis acid, for example one of the reagents described above such as 4-(N-dimethylamino)pyridine, the reaction suitably taking place in the presence of an organic solvent, for example a polar solvent such as pyridine or acetonitrile, or a hydrocarbon solvent, for example toluene or xylene, or a halogenated hydrocarbon, for example dichloromethane at a temperature in the range 20°-150° C.

Part C involves the formation of a compound of formula I wherein R is hydrogen. This reaction may be carried out by reacting a compound of formula V with hydroxylamine to give an intermediate oxime derivative of formula I wherein $R^2$ represents hydrogen, and reacting said oxime derivative with a compound of formula $R^2$-L, wherein $R^2$ is as defined above for formula I and L is a leaving group such as, for example, chloride, bromide, iodide, sulphate, nitrate, methyl sulphate, ethyl sulphate, tetrafluoroborate, hexafluorophosphate, hexafluoroantimonate, methanesulphonate, fluorosulphonate, fluoromethanesulphonate and trifluoromethanesulphonate, or, preferably, by reacting a compound of formula V with a derivative of formula $H_2N—O—R^2$ (or a salt thereof, such as the hydrochloride salt together with a base such as triethylamine) where $R^2$ is as defined for formula I.

Oximation suitably takes place at a temperature in the range 0° to 50° C., conveniently at ambient temperature, optionally in the presence of water and/or an organic solvent, suitably an alcohol, for example methanol or ethanol, and optionally, if the salt of $H_2N—O—R^2$ is used, in the presence of a base, suitably an amine base such as triethylamine.

An optional step, Part D, involves the replacement of the hydrogen atom (formula I where R is hydrogen) with an alternative substituent of the type defined above for R in formula I. Such replacement may occur in standard manner, by reaction with a suitable compound R-L, where L is a leaving group as defined above, or with an inorganic or organic base or salt, suitably at a temperature in the range 0°-100° C., preferably 20°-50° C., in the presence of an organic solvent and/or water.

A compound of formula V may be converted into another compound of formula V by substitution of the phenyl ring, for example by sulphonation, and/or by derivatisation using standard techniques.

Intermediate compounds of formula V are novel and therefore a further embodiment of the invention provides such novel compounds, and their preparation.

Compounds of formula I have been found to show interesting activity as herbicides, showing high activity against undesirable grasses, such as blackgrass, wild oats, annual meadow grass, Red Fescue and barnyard grass, whilst low or no activity against useful, non-target species, including linseed, mustard, sugar beet, rape and soya, and some selectivity to small grain cereals. Accordingly, the invention further provides a herbicidal, especially graminicidal, composition comprising a compound of formula I as defined above in association with at least one carrier, and a method of making such a composition, which comprises bringing a compound of formula I into association with at least one carrier.

The invention also provides the use of such a compound or composition according to the invention as a herbicide, especially as a graminicide. Further, in accordance with the invention there is provided a method of combating undesired plant growth at a locus by treating the locus with a compound or composition according to the invention. The locus may for example be a crop area in which the compound selectively combats weed growth. Application to the locus may be pre-emergence or post-emergence. The dosage of active ingredient used may, for example, be from 0.01 to 10 kg/ha, preferably 0.05 to 4 kg/ha. A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or aralipahtic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension conentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties. It is to be expected that certain mixtures will give synergistic effects.

The invention will now be further described with reference to the accompanying Examples. Examples 1 to 38 relate to the preparation of precursors and the remaining Examples relate to the preparation of compounds of formula I. Structures of compounds were confirmed by mass spectrometry and nuclear magnetic resonance analysis.

EXAMPLE 1

Preparation of 5,5-dimethyl-4-phenyl cyclohexane-1,3-dione

A mixture of ethyl phenyl acetate (34 g) and mesityl oxide (20 g) was added to a solution of sodium (4.6 g) in ethanol (80 ml) and the solution was refluxed for 4 hours. The ethanol was evaporated in vacuo, water was added to the residue and the aqueous solution was extracted with diethyl ether. The aqueous phase was acidified with concentrated hydrochloric acid and the product was extracted with methylene chloride. Evaporation of the extract and purification of the residue on a silica-gel column using 5% (v/v) methanol-methylene chloride as eluant gave the title compound (24 g) as a white solid of melting point 133°–135° C.

| Analysis: | |
|---|---|
| Calculated for $C_{14}H_{16}O_2$: | C 77.8; H 7.4% |
| Found: | C 77.6; H 7.2% |

The following precursor compounds of formula VII, set out in Table 1, were prepared in the manner of the compound of Example 1.

butyryloxy-5,5-dimethyl-6-phenyl cyclohex-1-ene-3-one. Toluene (100 ml) was added, followed by 4-(N-dimethylamino) pyridine (1 g) and the mixture was

TABLE 1

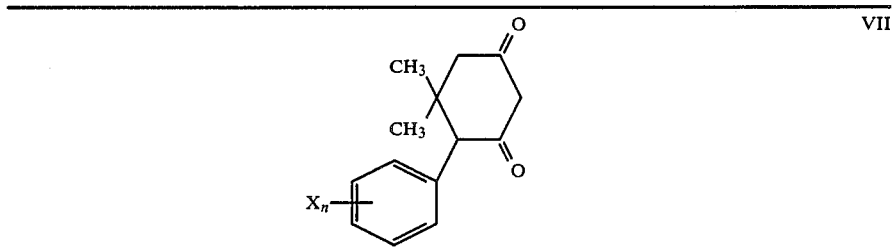

VII

| Example No. | $X_n$ | Analysis | | | | m.p. (°C.) |
|---|---|---|---|---|---|---|
| | | C Calc. % | C Found % | H Calc. % | H Found % | |
| 2 | 2,4-di-Cl | 58.9 | 58.5 | 4.9 | 4.8 | 109–110 |
| 3 | 4-Cl | 67.0 | 66.3 | 6.0 | 6.0 | 165–167 |
| 4 | 2-Me | 78.2 | 76.7 | 7.8 | 7.4 | 201–205 |
| 5 | 2-Cl | 67.0 | 66.4 | 5.9 | 6.0 | 165–168 |
| 6 | 3,4-di-MeO— | 69.5 | 67.1 | 7.2 | 6.9 | 50–52 |
| 7 | 4-F | 71.8 | 71.3 | 6.4 | 6.5 | 164–166 |
| 8 | 3,4-methylenedioxy | 69.2 | 69.6 | 6.2 | 6.5 | Note 1 |
| 9 | 4-Me | 78.3 | 77.9 | 7.8 | 7.9 | 153–154 |
| 10 | 2-F | 71.8 | 73.0 | 6.4 | 6.8 | 53–55 |
| 11 | 3-Me | 78.3 | 78.0 | 7.8 | 7.8 | 155–158 |
| 12 | 3-Cl | 67.2 | 66.7 | 6.0 | 6.7 | 158–160 |
| 13 | 3-MeO | 73.2 | 72.7 | 7.3 | 7.2 | 134–135 |
| 14 | 3-CF$_3$ | 63.4 | 60.6 | 5.3 | 4.8 | 62–64 |

Note 1. m/e 260/260 (m.p. not recorded)

EXAMPLE 15

Preparation of 2-butyryl-5,5-dimethyl-3-hydroxy-4-phenylcyclohex-2-ene-1-one

Triethylamine (5.2 g) was added dropwise to a stirred solution of 5,5-dimethyl-4-phenyl cyclohexane-1,3-dione (10.8 g) and n-butyryl chloride (5.3 g) in methylene chloride (100 ml). After stirring at ambient temperature for a further 2 hours, the reaction solution was washed with water and brine and dried over anhydrous magnesium sulphate. The methylene chloride was removed in vacuo to give a mixture of 1-butyryloxy-5,5-di-methyl-4-phenyl cyclohex-1-ene-3-one and 1-butyryloxy-5,5-dimethyl-6-phenyl cyclohex-1-ene-3-one. Toluene (100 ml) was added, followed by 4-(N-dimethylamino) pyridine (1 g) and the mixture was refluxed for 3 hours. Evaporation of the toluene in vacuo gave a red oil which was purified on a silica gel column using 5% (v/v) diethyl ethermethylene chloride as eluant to give the title compound (6 g) as a pale yellow oil.

| Analysis: | |
|---|---|
| Calculated for C$_{18}$H$_{22}$O$_3$: | C 75.5; H 7.7% |
| Found: | C 75.7; H 7.7% |

The following precursor compounds of formula VIII, set out in Table 2, where made in the manner of the compound of Example 15.

TABLE 2

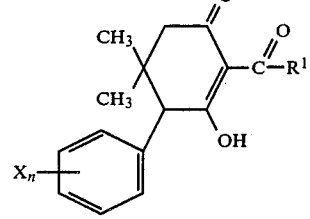

(VIII)

| Example No. | $X_n$ | $R^1$ | Analysis | | | | m.p. (°C.) |
|---|---|---|---|---|---|---|---|
| | | | C Calc. % | C. Found % | H Calc. % | H Found % | |
| 16 | H | Et | 75.0 | 75.8 | 7.3 | 7.2 | oil |
| 17 | 2,4-di-Cl | Et | 59.8 | 59.6 | 5.3 | 5.2 | 109–110 |
| 18 | 2,4-di-Cl | 2,4-dichlorobenzyl | 55.9 | 55.5 | 3.8 | 3.8 | 130–131 |
| 19 | 4-Cl | Et | 66.6 | 67.0 | 6.2 | 6.2 | 92–94 |
| 20 | 4-Cl | n-Pr | 67.3 | 67.4 | 6.5 | 6.5 | oil |
| 21 | 2-Me | Et | 75.5 | 74.0 | 7.6 | 7.6 | 74–76 |
| 22 | 2-Cl | Et | 66.5 | 67.4 | 6.2 | 6.2 | 67–69 |
| 23 | 2-Cl | n-Pr | 67.1 | 66.2 | 6.5 | 6.6 | 54–55 |
| 24 | 2,4-diCl | n-Pr | 60.8 | 59.4 | 5.6 | 5.7 | oil |
| 25 | H | Me | 74.4 | 73.9 | 7.0 | 7.1 | oil |
| 26 | 4-F | Et | 70.3 | 67.0 | 6.6 | 6.7 | oil |
| 27 | 3,4-methylenedioxy | Et | 68.4 | 66.8 | 6.3 | 6.3 | oil |

TABLE 2-continued

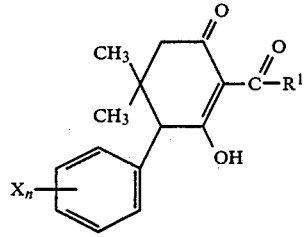

(VIII)

| Example No. | $X_n$ | $R^1$ | C Calc. % | C. Found % | H Calc. % | H Found % | m.p. (°C.) |
|---|---|---|---|---|---|---|---|
| 28 | 3,4-methylenedioxy | $^n$Pr | 69.1 | 66.9 | 6.7 | 6.6 | oil |
| 29 | 4-Me | Et | 75.5 | 73.9 | 7.7 | 8.1 | oil |
| 30 | 2-F | Et | 70.3 | 69.9 | 6.6 | 6.5 | oil |
| 31 | 3-Me | Et | 75.5 | 75.6 | 7.7 | 8.0 | oil |
| 32 | 3-MeO | $^n$Pr | 60.1 | 60.6 | 7.6 | 7.9 | oil |
| 33 | 3-Cl | Et | 66.7 | 66.8 | 6.2 | 6.2 | 77–78 |
| 34 | 3,4-di-MeO— | Et | 68.6 | 68.7 | 7.2 | 7.2 | 50–52 |
| 35 | 3-Me | Me | 75.0 | 75.0 | 7.4 | 7.4 | 105–107 |
| 36 | 3-Me | $^n$Pr | 76.0 | 74.4 | 8.0 | 7.9 | oil |
| 37 | 4-SO$_2$NMe$_2$ | Et | 60.2 Note 1 | 58.7 | 6.6 | 6.6 | 56–57 |
| 38 | 3-CF$_3$ | $^n$Pr | 64.4 | 62.6 | 5.9 | 6.4 | oil |

Note 1 N Calc. % 3.7 Found % 4.3

EXAMPLE 39

Preparation of 2-[1-(allyloxyimino)butyl]-5,5-dimethyl-3-hydroxy-4-phenyl cyclohex-2-ene-1-one Triethylamine (1.2 g) was added to a solution of 2-butyryl-5,5-dimethyl -3-hydroxy-4-phenyl cyclohex-2-ene-1-one (2.8 g) and O-allylhydroxylamine hydrochloride (1.2 g) in ethanol (50 ml). After stirring at ambient temperature overnight, the ethanol was evaporated in vacuo, water was added to the residue and the aqueous solution extracted with methylene chloride. After drying the organic extracts over anhydrous magnesium sulphate, the methylene chloride was evaporated in vacuo. The residue was chromatographed on a silica gel column using 5% (v/v) diethyl ether-methylene chloride as eluant to give the title compound (2.1 g) as a viscous, colourless oil.

| Analysis: | |
|---|---|
| Calculated for C$_{21}$H$_{27}$NO$_3$: | C 73.9; H 7.9; N 4.1% |
| Found: | C 74.7; H 7.8; N 4.3% |

The following compounds of formula IX, set out in Table 3 below, were made in the manner of the compound of Example 39.

TABLE 3

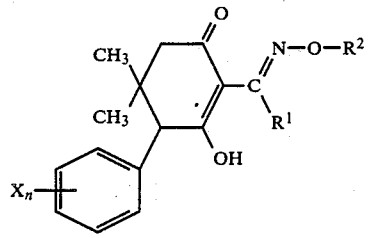

IX

| Ex. No. | $X_n$ | $R^1$ | $R^2$ | C Calc. % | C Found % | H Calc. % | H Found % | N Calc. % | N Found % | m.p. (°C.) |
|---|---|---|---|---|---|---|---|---|---|---|
| 40 | H | n-Pr | Et | 72.9 | 73.2 | 8.2 | 8.5 | 4.2 | 4.0 | oil |
| 41 | H | Et | allyl | 73.4 | 73.1 | 7.6 | 7.6 | 4.3 | 4.6 | oil |
| 42 | H | Et | Et | 72.4 | 72.0 | 7.9 | 8.0 | 4.4 | 4.4 | oil |
| 43 | H | benzyl | allyl | 77.1 | 77.0 | 6.9 | 7.1 | 3.6 | 3.9 | oil |
| 44 | H | benzyl | Et | 76.4 | 75.9 | 7.2 | 7.3 | 3.7 | 3.8 | oil |
| 45 | 2,4-diCl | n-Pr | allyl | 61.4 | 61.1 | 6.1 | 6.2 | 3.4 | 3.8 | oil |
| 46 | 4-Cl | Et | allyl | 66.4 | 66.6 | 6.6 | 6.7 | 3.9 | 3.9 | oil |
| 47 | 4-Cl | Et | Et | 65.2 | 64.5 | 6.9 | 7.0 | 4.0 | 4.8 | oil |
| 48 | 4-Cl | n-Pr | allyl | 67.1 | 67.1 | 6.9 | 7.1 | 3.7 | 3.7 | oil |
| 49 | 4-Cl | n-Pr | Et | 66.0 | 66.3 | 7.2 | 7.2 | 3.9 | 4.1 | oil |
| 50 | 2-Cl | Et | allyl | 66.4 | 65.4 | 6.6 | 6.7 | 3.9 | 4.0 | oil |
| 51 | 2-Cl | Et | Et | 65.2 | 64.5 | 6.9 | 7.0 | 4.0 | 4.1 | oil |
| 52 | 2-Cl | n-Pr | allyl | 67.1 | 66.8 | 6.9 | 6.8 | 3.7 | 4.3 | oil |
| 53 | 2-Cl | n-Pr | Et | 66.0 | 65.9 | 7.2 | 7.2 | 3.8 | 3.6 | oil |
| 54 | 2-Me | Et | allyl | 73.9 | 73.4 | 7.9 | 7.8 | 4.1 | 4.2 | oil |
| 55 | 2-Cl | Et | —CH$_2$—CH=CHCl | 60.6 | 57.5 | 5.8 | 5.7 | 3.5 | 3.6 | oil |

TABLE 3-continued

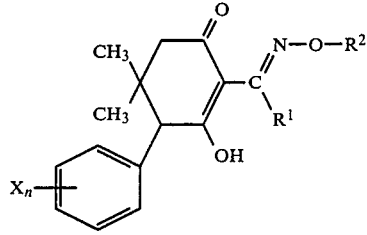

IX

| Ex. No. | $X_n$ | $R^1$ | $R^2$ | C Calc. % | C Found % | H Calc. % | H Found % | N Calc. % | N Found % | m.p. (°C.) |
|---|---|---|---|---|---|---|---|---|---|---|
| 56 | 3,4-di-MeO | Et | Et | 67.2 | 64.0 | 7.7 | 7.6 | 3.7 | 3.3 | oil |
| 57 | 3,4-di-MeO | Et | allyl | 68.2 | 64.2 | 7.5 | 7.2 | 3.6 | 3.7 | oil |
| 58 | 2-Cl | $^n$Pr | $-CH_2-C(CH_3)-CH_2$ | 67.1 | 68.2 | 7.4 | 7.4 | 3.7 | 3.8 | oil |
| 59 | 2-Cl | $^n$Pr | $-CH_2-CH=CHCl$ trans | 61.4 | 59.4 | 6.1 | 7.0 | 3.4 | 3.1 | oil |
| 60 | H | Me | allyl | 72.8 | 71.0 | 7.4 | 7.3 | 4.5 | 4.1 | oil |
| 61 | 4-F | Et | Et | 68.5 | 66.0 | 7.2 | 7.1 | 4.2 | 4.2 | oil |
| 62 | 4-F | Et | allyl | 69.6 | 68.9 | 7.0 | 7.1 | 4.1 | 4.2 | oil |
| 63 | 4-F | Et | $-CH_2-CH=CHCl$ trans | 63.2 | 60.1 | 6.1 | 5.4 | 3.7 | 3.7 | oil |
| 64 | 4-F | Et | $-CH(CH_3)-CH=CH_2$ | 70.2 | 70.3 | 7.2 | 7.3 | 3.9 | 3.9 | oil |
| 65 | 4-F | Et | $-CH_2-C(CH_3)=CH_2$ | 70.2 | 69.5 | 7.2 | 7.4 | 3.9 | 4.5 | oil |
| 66 | 3,4-methylenedioxy- | Et | Et | 66.9 | 66.8 | 7.0 | 7.0 | 3.9 | 3.8 | oil |
| 67 | 3,4-methylenedioxy- | Et | allyl | 67.9 | 67.0 | 6.7 | 6.7 | 3.8 | 4.1 | oil |
| 68 | 3,4-methylenedioxy- | $^n$Pr | Et | 67.6 | 66.0 | 7.2 | 7.2 | 3.8 | 3.8 | oil |
| 69 | 3,4-methylenedioxy- | $^n$Pr | allyl | 68.6 | 68.3 | 7.0 | 7.3 | 3.6 | 3.8 | oil |
| 70 | 4-Me | Et | Et | 73.0 | 69.8 | 8.2 | 7.9 | 4.3 | 4.6 | oil |
| 71 | 4-Me | Et | allyl | 74.0 | 73.5 | 7.9 | 7.8 | 4.1 | 4.1 | oil |
| 72 | 2-F | Et | allyl | 69.8 | 69.5 | 7.0 | 7.0 | 4.1 | 4.0 | oil |
| 73 | 2-F | Et | Et | 68.5 | 68.1 | 7.2 | 7.5 | 4.2 | 4.2 | oil |
| 74 | 2,4-di-Cl | $^n$Pr | $-CH_2CH=CHCl$ cis/trans | 56.7 | 56.2 | 5.4 | 5.6 | 3.1 | 3.2 | oil |
| 75 | 4-Cl | Et | $-CH_2CH=CHCl$ cis/trans | 60.6 | 58.8 | 5.8 | 5.7 | 3.5 | 3.8 | oil |
| 76 | 3-Me | Et | allyl | 73.9 | 70.1 | 7.9 | 7.6 | 4.1 | 4.2 | oil |
| 77 | 3-Me | Me | allyl | 73.4 | 72.0 | 7.6 | 7.7 | 4.3 | 4.3 | 71–73 |
| 78 | 3-Me | $^n$Pr | allyl | 74.4 | 73.2 | 8.2 | 8.1 | 3.9 | 3.9 | oil |
| 79 | 3-Cl | Et | allyl | 66.5 | 65.2 | 6.6 | 6.6 | 3.9 | 3.8 | oil |
| 80 | 4-SO$_2$NMe$_2$ | Et | allyl | 60.8 | 57.9 | 6.9 | 6.7 | 6.5 | 6.3 | oil |
| 81 | 3-MeO | $^n$Pr | allyl | 71.1 | 69.8 | 7.8 | 7.8 | 3.8 | 4.0 | oil |
| 82 | 3-CF$_3$ | $^n$Pr | allyl | 64.5 | 64.7 | 6.3 | 6.3 | 3.4 | 3.4 | oil |

EXAMPLE 83

Preparation of Tetra-n-butylammonium salt of 2-[1-(alkyloxyiminopropyl]-3-hydroxy-4-(3-methylphenyl)-5,5-dimethyl-cyclohex-2-ene-1-one 2-[1-(allyloxyimino)-propyl]-3-hydroxy-4-(3-methylphenyl)-5,5-dimethyl-cyclohex-2-ene-1-one (2 g) in methanol (2 ml) was added to a 25% solution of tetra-n-butylammonium hydroxide (20 ml). After standing at room temperature overnight, the methanol was evaporated in vacuo. Methylene chloride was added to the residue, the solution washed with water, dried over anhydrous magnesium sulphate, filtered and evaporated to give the title compound as a colourless oil. (3 g)

| Analysis: | |
|---|---|
| Calculated for C$_{37}$H$_{62}$N$_2$O$_3$: | C 76.3; H 10.7; N 4.8% |
| Found: | C 71.4; H 10.1; N 4.4% |

EXAMPLE 84

Preparation of 2-[1-(allyoxyimino)propyl]-3-acetoxy-4-(3-methylphenyl)-5,5-dimethyl-cyclohex-2-en-1-one Triethylamine (1.1 ml) in methylene chloride (20 ml) was added dropwise to a solution of 2-[1-(allyloxyimino)propyl]-3-hydroxy-4-(3-methylphenyl)-5,5-dimethyl-cyclohex-2-en-1-one (2.1 g) and acetyl chloride (0.6 ml) in methylene chloride (100 ml). After stirring at ambient temperature overnight, the solution was washed with water, dried over anhydrous magnesium sulphate, filtered and evaporated. The residue was purified on a silica gel 0 column using methylene chloride as eluant to give the title compound (0.8 g) as a colourless oil.

| Analysis: | |
|---|---|
| Calculated for $C_{23}H_{29}O_4N$: | C 72.1; H 7.6; N 3.7% |
| Found: | C 69.7; H 7.6; N 3.5% |

EXAMPLE 85

Preparation of Sodium salt of 2-[1-(allyloxyimino)propyl]-3-hydroxy-4-(3-chlorophenyl)-5,5-dimethylcyclohex-2-en-1-one 2-[1-(allyloxyimino)-propyl]-3-hydroxy-4-(3-chlorophenyl)-5,5-dimethyl-cyclohex-2-en-1-one (1.7 g) was added to a solution of sodium hydroxide (0.2 g) in ethanol (30 ml) at ambient temperature. After stirring for 30 minutes, the ethanol was evaporated and the residue triturated with diether ether to give the title compound as a white solid. (1.0 g) of m.p. 160° C.

| Analysis: | |
|---|---|
| Calculated for $C_{20}H_{23}O_3NClNa$: | C 62.6; H 6.0; N 3.7% |
| Found: | C 57.4; H 6.2; N 3.8% |

EXAMPLE 86

Preparation of 2-[1-(allyloxyimino)propyl]-3-benzoyloxy-4-(3-chlorophenyl)-5,5-dimethyl-cyclohex-2-en-1-one Aqueous 1% sodium hydroxide (30 ml) was added to a stirred solution of 2-[1-(allyloxyimino)propyl-3-hydroxy-4-(3-chlorophenyl)-5,5-dimethyl-cyclohex-2-en-1-one (2.5 g) in acetone (200 ml). The mixture was stirred at ambient temperature for 5 minutes and then benzoyl chloride (1 g) in acetone (25 ml) was added dropwise. After 30 minutes the mixture was evaporated in vacuo and the residue purified on a silica gel column using methylene chloride as eluant to give the title compound (3.0 g) as a colourless oil.

| Analysis | |
|---|---|
| Calculated for $C_{27}H_{28}O_4NCl$: | C 69.7; H 6.0; N 3.0% |
| Found: | C 69.4; H 6.0; N 3.3% |

Herbicidal Activity

To evaluate their herbicidal activity, compounds according to the invention were tested using a representative range of plants: maize, *Zea mays* (Mz); rice, *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 900 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale, a rating 0 indicating growth as untreated control, and a rating 9 indicating death. An increase of 1 unit on the linear scale approximates to a 10% increase in the level of effect.

The results of the tests are set out in Table IV below, in which the compounds are identified by reference to the preceding examples. A blank space in Table IV below corresponds to a rating 0.

TABLE IV

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 39 | 8 | 8 | 9 | 9 | | 3 | 2 | | 5 | 8 | 6 | 9 | 8 | | 3 | | | 6 | 8 | 9 | 7 | | | | |
| | | | | | | | | | 1 | 5 | 1 | 9 | 7 | | | | | 2 | 4 | 7 | 5 | | | | |
| 40 | 3 | 8 | 8 | 7 | | 2 | 2 | | 5 | 3 | 6 | 9 | 7 | | 2 | | | 0 | 8 | 9 | 7 | | | | |
| | | | | | | | | | 1 | 1 | 2 | 9 | 6 | | | | | 0 | 5 | 6 | 6 | | | | |
| 41 | 7 | 7 | 8 | 7 | | 5 | 1 | | 5 | 8 | 7 | 9 | 8 | 2 | 5 | 4 | 3 | 5 | 8 | 9 | 8 | | 3 | 3 | |
| | | | | | | | | | 1 | 5 | 6 | 8 | 7 | 1 | 4 | 1 | 1 | 3 | 2 | 8 | 6 | | | 1 | |
| 42 | 4 | 6 | 7 | 3 | 2 | 3 | 3 | | 5 | 4 | 4 | 8 | 6 | 3 | 5 | 3 | 0 | 5 | 7 | 9 | 6 | | 3 | 2 | |
| | | | | | | | | | 1 | 3 | 3 | 7 | 6 | 1 | 3 | | | 0 | 0 | 8 | 2 | | | | |
| 43 | 1 | 1 | 4 | 2 | | | | | 5 | 4 | 4 | 7 | 6 | | 2 | | | 2 | 2 | 5 | 6 | | | | |
| | | | | | | | | | 1 | 3 | 1 | 4 | 1 | | | | | | | | | | | | |
| 44 | | | | | | 4 | 2 | | 5 | | 1 | 2 | 2 | | | | | 3 | 8 | 9 | 5 | | 1 | | |
| | | | | | | | | | 1 | | 1 | | | | | | | | | 2 | | | | | |
| 45 | | | | | | | | | 5 | 8 | 1 | 1 | 5 | | | | | | | | | | | | |
| | | | | | | | | | 1 | 6 | | | | | | | | | | | | | | | |
| 46 | | 2 | 2 | | | | | | 5 | 6 | 3 | 2 | 4 | 2 | 2 | | | | | 5 | | | | | |

TABLE IV-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 47 | | | 2 | | | | | | 1 | | 3 | 1 | | | 1 | 1 | | | | | | | | | |
| | | | | | | | | | 5 | | 4 | 3 | | 3 | | 1 | | | | 3 | | | | | |
| 48 | | 3 | 2 | 3 | | | | | 1 | | 3 | 2 | 1 | | | | | | | | | | | | |
| | | | | | | | | | 5 | 4 | 2 | 5 | 5 | | 2 | | 2 | | | 7 | | | | | |
| 49 | | | 3 | | | | | | 1 | 2 | 1 | 3 | 2 | | 1 | | | | | | | | | | |
| | | | | | | | | | 5 | | | 5 | 3 | | 4 | | 2 | | | 3 | | | | | |
| 50 | 6 | 2 | 6 | 3 | | 1 | 2 | | 1 | | | 3 | 2 | | 1 | | | | | | | | | | |
| | | | | | | | | | 5 | 6 | 6 | 8 | 7 | 3 | 2 | 2 | 2 | 3 | 5 | 8 | 5 | | | | |
| 51 | | | 4 | | | | | 3 | 1 | 3 | 2 | 7 | 3 | | | 1 | | 1 | 1 | 4 | 2 | | | | |
| | | | | | | | | | 5 | 3 | | 6 | | | | | 2 | | 2 | 5 | | | | | |
| 52 | 7 | 4 | 9 | 6 | | | | | 1 | | | 3 | | | | | | | | 1 | | | | | |
| | | | | | | | | | 5 | 8 | 6 | 9 | 8 | | | | 3 | 7 | 7 | 9 | 6 | | | | |
| 53 | 2 | 3 | 8 | | | | | | 1 | 7 | 2 | 8 | 7 | | | | | 2 | 1 | 7 | 2 | | | | |
| | | | | | | | | | 5 | 4 | 6 | 8 | 1 | 3 | 3 | 2 | 2 | 1 | 7 | 8 | 6 | | | | |
| 54 | 7 | 5 | 8 | 7 | | 2 | | | 1 | 2 | 3 | 8 | | | | | | | | 6 | 1 | | | | |
| | | | | | | | | | 5 | 8 | 7 | 8 | 8 | 2 | | 1 | 3 | 7 | 8 | 9 | 7 | | | | 2 |
| 55 | | | | | | | | | 1 | 6 | 3 | 8 | 8 | | | | | 3 | 3 | 8 | 6 | | | | |
| | | | | | | | | | 5 | 2 | | 3 | | | 2 | 3 | 2 | | | | | | | | |
| 56 | | 2 | 3 | | 2 | | | | 1 | 1 | | 2 | | | | 1 | | | | | | | | | |
| | | | | | | | | | 5 | 2 | 2 | 8 | | | 2 | | | | | 2 | 7 | | | | |
| 57 | | 4 | 3 | | 1 | | | | 1 | | | 4 | | | | | | | | | | | | | |
| | | | | | | | | | 5 | 5 | 5 | 8 | 2 | | | | | 2 | 5 | 7 | 3 | | | | |
| 58 | 3 | | 6 | | | | | | 1 | 2 | 1 | 4 | | | | | | | | | | | | | |
| | | | | | | | | | 5 | 4 | | 7 | 3 | | 2 | 4 | | | 3 | 3 | 3 | | | | |
| 59 | 2 | | 6 | 5 | | | 2 | | 1 | 2 | | 6 | 2 | | | | | | | | 1 | | | | |
| | | | | | | | | | 5 | 2 | | 6 | 4 | | | 4 | 2 | | 6 | 6 | 4 | | | | |
| 60 | 7 | 8 | 9 | 7 | | 3 | 3 | | 1 | 1 | | 6 | 3 | | | 1 | | | 4 | 2 | 2 | | | | |
| | | | | | | | | | 5 | 7 | 6 | 9 | 8 | 3 | 5 | 6 | 2 | 3 | 8 | 8 | 6 | | 2 | | 3 |
| 61 | 5 | 4 | 7 | | 2 | 3 | 3 | 2 | 1 | 5 | 3 | 8 | 7 | | 2 | 2 | | 2 | 5 | 8 | 1 | | | | |
| | | | | | | | | | 5 | 5 | | 8 | 8 | 4 | 4 | 5 | /3 | 6 | 7 | 9 | 5 | 3 | | | |
| 62 | 7 | 7 | 8 | 7 | | 4 | 3 | 3 | 1 | 4 | | 8 | 7 | 2 | 3 | 3 | 1 | | | 6 | 2 | | | | |
| | | | | | | | | | 5 | 8 | 7 | 9 | 9 | 4 | 6 | 5 | 3 | 5 | 9 | 9 | 8 | | 3 | | 2 |
| 63 | 4 | | 8 | 2 | | | 3 | 2 | 1 | 6 | 2 | 9 | 8 | 2 | 3 | 2 | 1 | 2 | 2 | 8 | 0 | | | | |
| | | | | | | | | | 5 | 5 | 1 | 8 | 5 | 3 | 4 | 4 | 1 | 2 | 5 | 8 | 5 | | | | |
| 64 | | | | | 2 | 3 | | | 1 | 3 | | 8 | 4 | | 1 | 1 | | | 2 | 4 | 2 | | | | |
| | | | | | | | | | 5 | 1 | | 8 | 5 | 3 | 5 | 4 | 3 | | | 3 | 2 | | | | |
| 65 | | | | | 2 | | | | 1 | 1 | | 7 | 2 | | 2 | 2 | 1 | | | 1 | | | | | |
| | | | | | | | | | 5 | 3 | 3 | 8 | 4 | 4 | 4 | 4 | 2 | | 4 | 4 | 1 | | | | |
| 66— | | 2 | 2 | 3 | | | | | 1 | 2 | | 8 | 3 | | | 1 | | | | | | | | | |
| | | | | | | | | | 5 | 4 | 4 | 8 | 6 | 2 | 2 | 2 | | 3 | 3 | 6 | 5 | | | | |
| 67 | | 2 | | 2 | | | | | 1 | 4 | 2 | 7 | 2 | | | | | 1 | | 2 | 1 | | | | |
| | | | | | | | | | 5 | 6 | 4 | 8 | 7 | | 2 | 3 | | 4 | 2 | 7 | 6 | | | | |
| 68 | 3 | 3 | 5 | 1 | | | | | 1 | 3 | 1 | 6 | | | | | | 1 | | 1 | | | | | |
| | | | | | | | | | 5 | 7 | 4 | 8 | 8 | 3 | 2 | | | 5 | 5 | 8 | 7 | | | | |
| 69 | 4 | 2 | 4 | 1 | | | | | 1 | 6 | | 7 | 5 | | | | | 2 | 2 | 4 | 4 | | | | |
| | | | | | | | | | 5 | 7 | 4 | 9 | 8 | 4 | 4 | 2 | | 6 | 6 | 8 | 7 | | | | |
| 70 | 2 | 1 | | | | | | | 1 | 4 | 1 | 7 | 6 | 1 | | | | .2 | 1 | 5 | 2 | | | | |
| | | | | | | | | | 5 | 5 | 3 | 8 | | | | | | | | 1 | 1 | | | | |
| 71 | | | | | | | | | 1 | 2 | | 4 | | | | | | | | | | | | | |
| | | | | | | | | | 5 | 5 | 2 | 8 | 4 | | | | | 1 | 2 | 2 | | | | | |
| 72 | 4 | 4 | 6 | 4 | | | | | 1 | 3 | | 5 | | | | | | | | | | | | | |
| | | | | | | | | | 5 | 7 | 6 | 8 | 8 | 3 | 6 | 4 | | 5 | 6 | 9 | 7 | 3 | 3 | | |
| 73 | | | 4 | | 6 | | | | 1 | 6 | 3 | 8 | 8 | | | | | 2 | 2 | 4 | 5 | | | | |
| | | | | | | | | | 5 | | 2 | 8 | | 2 | 7 | 4 | | 3 | 4 | 8 | 3 | | | 3 | 2 |
| 74 | | | | | | | | | 1 | | | 6 | | | | | | 2 | 1 | 5 | | | | | |
| | | | | | | | | | 5 | | | 3 | | 2 | 2 | 2 | | | | | | | | | |
| 75 | | | | | | | | | 1 | 2 | | 3 | | | 2 | 3 | 1 | | | | | | | | |
| | | | | | | | | | 5 | 1 | | 1 | | | | | | | | | | | | | |
| 76 | 7 | 5 | 7 | 6 | | | | | 1 | 8 | 5 | 8 | 8 | | | | 1 | 6 | 5 | 7 | 5 | | | | |
| | | | | | | | | | 5 | 7 | 3 | 8 | 5 | | | | | | | | 2 | | | | |
| 77 | 8 | 5 | 6 | 2 | | 4 | | | 1 | 8 | 6 | 8 | 5 | 2 | 2 | | 2 | 3 | 4 | 7 | 5 | | | | |
| | | | | | | | | | 5 | 6 | 2 | 7 | 2 | | | | | | | 1 | 2 | | | | |
| 78 | 8 | 8 | 9 | 9 | | | | | 1 | 9 | 8 | 9 | 9 | | | | | 4 | 8 | 9 | 7 | | | | |
| | | | | | | | | | 5 | 9 | 5 | 9 | 8 | | | | | 2 | 6 | 6 | 5 | | | | |
| 79 | 5 | 1 | 4 | 2 | 4 | 2 | | | 1 | 6 | 3 | 7 | 7 | | 5 | 3 | 2 | 2 | 5 | 5 | 5 | | | | |
| | | | | | | | | | 5 | 2 | 1 | 4 | 4 | | | | | | | 1 | 3 | | | | |
| 80 | 4 | 6 | 7 | 7 | 2 | 2 | | | 1 | 3 | 3 | 8 | 6 | | | | | | 4 | 5 | 7 | | | | |
| | | | | | | | | | 5 | 6 | 4 | 8 | 7 | | | | | | | 7 | 6 | | | | |
| 81 | 6 | 6 | 8 | 8 | | | | | 1 | 8 | 7 | 9 | 9 | | | | | 7 | 6 | 9 | 8 | | | | |
| | | | | | | | | | 5 | 1 | 6 | 4 | 8 | 7 | | | | | | 7 | 6 | | | | |
| 82 | | | | | | | | | 1 | 5 | 1 | 6 | 6 | 4 | 6 | 4 | 1 | | | 4 | | | | | |
| | | | | | | | | | 5 | 2 | | 3 | 1 | 3 | | | | | | 2 | | | | | |
| 83 | 6 | 2 | 5 | 3 | | | | | 1 | 5 | 3 | 8 | 5 | 1 | 2 | 1 | 3 | | | 2 | 3 | | | | |
| | | | | | | | | | 5 | 4 | 1 | 4 | | | | | | | | | 1 | | | | |
| 84 | 5 | 4 | 5 | 3 | | | | | 1 | 6 | 2 | 7 | | | 2 | | 2 | | 1 | 1 | 4 | | | | |
| | | | | | | | | | 5 | 4 | | 6 | | | | | | | | | 1 | | | | |
| 85 | 4 | | 3 | | 2 | 2 | | | 1 | 4 | 2 | 8 | 6 | 3 | 8 | 2 | | 2 | 5 | 4 | 6 | | | | |

TABLE IV-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 86 | | | | | | | | | 1<br>5<br>1 | 1<br>3<br>2 | | 6<br>7<br>4 | 5<br>2<br>2 | | | 1 | | | 1 | 2 | 2 | | | | |

We claim:

1. A compound of the formula

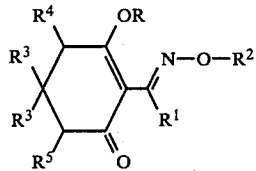

wherein
R is selected from a hydrogen atom, an optionally substituted alkyl group, an optionally substituted acyl group, a $C_{2-6}$ alkenyl group, a $C_{2-6}$ alkynyl group, and an organic or inorganic cation selected from alkali and alkaline earth metal ions, transition metal ions, and ammonium ions optionally substituted with 1–4 groups selected from optionally substituted alkyl, phenyl and phenylalky groups,
$R^1$ is selected from alkyl, haloalkyl, $C_{2-6}$ alkenyl, $C_{2-6}$ alkynyl, or an optionally substituted phenyl group,
$R^2$ is selected from cycloalkyl, $C_{2-6}$ alkenyl or haloalkyl, $C_{2-6}$ alkynyl, or an optionally substituted alkyl group,
$R^3$ is an optionally substituted alkyl group,
one of $R^4$ and $R^5$ represents a hydrogen atom or an alkyl group while the other of $R^4$ and $R^5$ represents an optionally substituted phenyl group,
said optional alkyl substituents being selected from the group consisting of halogen, $C_{1-6}$ alkoxy, $C_{1-6}$ alkylthio, ($C_{1-6}$ alkoxy)carbonyl and optionally substituted phenyl groups,
said optional phenyl substituents being selected from the group consisting of halogen, nitro, cyano, $C_{1-6}$ alkyl, $C_{1-6}$ haloalkyl, $C_{1-6}$ alkoxy, $C_{1-10}$ alkylene dioxy, $C_{1-6}$ alkylthio and $C_{2-6}$ alkenylthio and amino, acetamido, mono($C_{1-4}$) alkylamino and di($C_{1-4}$-alkyl)amino groups, and acyl groups,
said optionally substituted acyl group being selected from $C_{2-6}$ alkanoyl and optionally substituted benzoyl groups, sulphonyl groups, sulphonamido groups of the formula $SO_2NQ^1Q^2$ wherein each of $Q^1$ and $Q^2$ independently represents a hydrogen atom or an alkyl group.

2. The compound of claim 1 wherein R is hydrogen.

3. The compound of claims 1 or 2 wherein $R^1$ represents a $C_{1-6}$ alkyl or aralkyl group.

4. The compound of claim 1 wherein $R^2$ is selected from a $C_{1-6}$ alkyl group optionally substituted by halogen, an alkoxy group and $C_{2-6}$ alkenyl group optionally substituted by a halogen atom.

5. The compound of claim 1 wherein one of $R^4$ and $R^5$ independently represents a hydrogen atom and the other of $R^4$ and $R^5$ independently represents a phenyl group optionally substituted by 1–5 moieties independently selected from halogen, and $C_{1-6}$ alkyl, haloalkyl, alkoxy and alkylene dioxy groups, and a sulphonamido group.

6. The compound of claim 1 wherein each $R^3$ represents a methyl group.

7. A herbicidal composition comprising at least one carrier and herbicially-effective amount of a compound of formula (I) as defined in claim 1.

8. The composition of claim 7 wherein R is hydrogen.

9. The composition of claims 7 or 8 wherein $R^1$ represents a $C_{1-6}$ alkyl or aralkyl group.

10. The composition of claim 7 wherein $R^2$ is selected from a $C_{1-6}$ alkyl group optionally substituted by halogen, an alkoxy group and a $C_{2-6}$ alkenyl group optionally substituted by a halogen atom.

11. The composition of claim 7 wherein one of $R^4$ and $R^5$ independently represents a hydrogen atom and the other of $R^4$ an $R^5$ independently represents a phenyl group optionally substituted by 1–5 moieties independently selected from halogen, and $C_{1-6}$ alkyl, haloalkyl, alkoxy, and alkylene dioxy groups, and a sulphonamido group.

12. The composition of claim 7 wherein each $R^3$ represents a methyl group.

13. The composition of claim 7 wherein said compound is present in an amount in the range of 0.5 to 95% by weight.

14. A method of combating undesired plant growth at a locus comprising treating said locus with a herbicidally-effective amount of a compound of formula (I) as defined in claim 1.

15. The method of claim 14 wherein R is hydrogen.

16. The method of claims 14 or 15 wherein $R^1$ represents a $C_{1-6}$ alkyl or aralkyl group.

17. The method of claim 14 wherein $R^2$ is selected from a $C_{1-6}$ alkyl group optionally substituted by halogen, an alkoxy group and a $C_{2-6}$ alkenyl group optionally substituted by a halogen atom.

18. The method of claim 14 wherein on of $R^4$ and $R^5$ independently represents a hydrogen atom and the other of $R^4$ and $R^5$ independently represents a phenyl group optionally substituted by 1–5 moieties independently selected from halogen, and $C_{1-6}$ alkyl, haloalkyl, alkoxy, and alkylene dioxy groups, and sulphonamido group.

19. The method if claim 14 wherein each $R^3$ represents a methyl group.

20. The method of claim 14 wherein said compound is applied in the form of a herbicidal composition comprising at least one carrier.

21. The method of claim 14 wherein said compound is applied in a dosage of from 0.01 to 10 kg/ha.

* * * * *